United States Patent [19]

Dowben et al.

[11] 4,320,970
[45] Mar. 23, 1982

[54] PHOTON COUNTING FLUORIMETER

[76] Inventors: Robert M. Dowben, 7150 Eudora Dr., Dallas, Tex. 75230; James R. Bunting, 3146 Hudnall St., Dallas, Tex. 75235

[21] Appl. No.: 809,138

[22] Filed: Jun. 22, 1977

Related U.S. Application Data

[63] Continuation of Ser. No. 634,796, Nov. 24, 1975, abandoned.

[51] Int. Cl.³ ............................................. G01N 21/64
[52] U.S. Cl. ................................... 356/317; 250/458; 250/459; 356/323; 356/417
[58] Field of Search ........... 250/458, 459, 460, 461 R, 250/461 B; 356/85, 93, 95, 98, 317, 318

[56] References Cited

U.S. PATENT DOCUMENTS

| 3,738,755 | 6/1973 | Chaney et al. | 356/117 |
| 3,832,555 | 8/1974 | Ohnishi | 250/458 |
| 3,854,050 | 12/1974 | Peterson et al. | 250/461 B |
| 3,886,363 | 5/1975 | Ohnishi et al. | 356/98 |
| 3,897,155 | 7/1975 | Smythe | 356/85 |
| 3,903,422 | 9/1975 | Buhrer | 250/461 R |

Primary Examiner—Vincent P. McGraw

Attorney, Agent, or Firm—Seidel, Gonda, Goldhammer & Panitch

[57] ABSTRACT

An ultraviolet light beam is split into two beams which are directed toward a reference cell and a sample cell, respectively. A mechanical rotating light chopper permits the reference and sample cells to be alternately illuminated. Radiation from the reference and sample cells is directed toward and sensed by a single photomultiplier tube. An up/down counter counts the number of photons impinging on the photomultiplier tube from the reference and sample cells. Photodiodes in conjunction with the mechanical light chopper cause the up/down counter to count up when photons are arriving from the sample cell and cause the up/down counter to count down when photons are arriving from the reference cell. A source intensity monitor prohibits further measurements after a preselected amount of incident flux has been sensed. The intensity monitor includes a photodetector circuit which senses a portion of the incident light. Pulses from the detector are fed to a counter and the number in the counter is compared to a preselected number which is set on a thumbwheel switch. When the comparison condition is met, the up/down counter of the fluorimeter is stopped.

4 Claims, 1 Drawing Figure

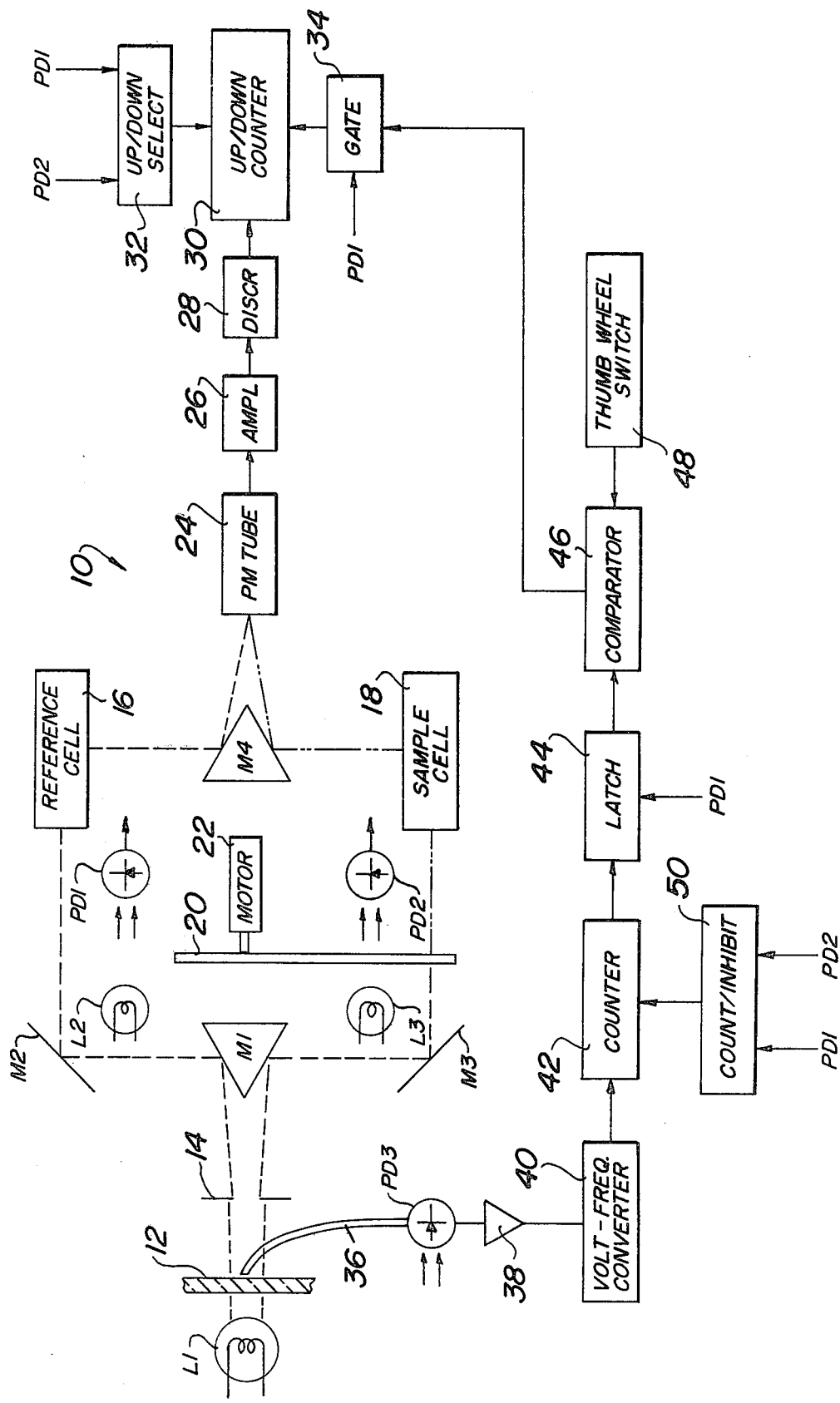

PHOTON COUNTING FLUORIMETER

This is a continuation of application Ser. No. 634,796, filed Nov. 24, 1975, now abandoned.

The present invention is directed toward a photon counting fluorimeter and more particularly toward a double beam photon counting fluorimeter capable of performing accurate, stable, reproducible measurements of extremely low fluorescent light intensities in the presence of large contributions of extraneous fluorescence and scattering of incident light. The invention is particularly useful for determining the concentration of fluorescent substances in complex mixtures. Specific applications of the device of the present invention are described in copending application Ser. No. 634,797, now abandoned, filed concurrently with the present application by the same inventors and incorporated herein by reference.

One of the essential problems in substantially all chemical or physical applications of analytical chemical methods, is the determination of the concentration of a substance in a mixture. This requires one to depend on the chemical or physical properties of the substance which define its identity, and hopefully allows a linear relationship between its concentration and some physical property. Analysis is usually relatively simple providing that the substance under consideration is found as a major fraction of the mixture, i.e. occurs in relative abundance, $10^{-6}$ M or higher. When concentrations of the unknown substance are lower, detection of the signal generated by the substance under analysis is limited by the nature of the signal detected and the method of detection.

The instrument constructed in accordance with the present invention is capable of measuring the fluorescence of a substance when it is found in concentrations as low as $10^{-12}$ M. The instrument is also particularly useful for the analysis of material in mixtures which contain other fluorescent species. In order to accomplish this, means are provided for removing unwanted fluorescent signals from the fluorescent signal to be measured. Furthermore, since the method of fluorescent analysis performed by the present invention uses a source of incident visible or ultraviolet illumination, scattering of this radiation by the sample into the detector adds signal which is not wanted. At low fluorescent signal levels the scattering intensity can seriously obscure the wanted signal in the noise of the scattering radiation. The problem of extracting a small signal of the fluorophore of interest from the large amount of noise associated with other fluorescence and scattering is mainly a problem of statistical manipulation of the data, either analytically or experimentally. The present invention handles the signal to noise problem by a combination of both forms of manipulation through the use of single event statistical counting of both the fluorescent and noise signals.

The standard prior art method of obtaining fluorescent intensity information is to use a photomultiplier tube whose anode current is amplified by normal analog circuits. In current amplification the unitary events of photons reaching the photocathode of the photomultiplier tube are averaged over a period of time; the unitary nature of each photon detected is therefore lost by the averaging process. The end result is that the amplification yields a current which fluctuates as a result of instabilities of the electronics and the fluorescent signal.

To subtract two such fluctuating signals, one being signal plus noise the other noise, from one another to a high degree of confidence with analog systems is a complex problem and depends on many variables having to do with the electronics and time of signal integration. At very low light levels the photocurrent generated by an analog system is also low and the statistics per unit time have a large deviation associated with them.

On the other hand, with photon counting techniques each photon reaching the photocathode produces a current pulse. The leading edge of this pulse, after amplification, can be discriminated and for each pulse received an event can be recorded. In this way the number of pulses received over the duration of an experiment will be known. This allows for unitary event statistics to be applied to the data, the deviation of the signal being the square root of the number of counts received. Knowing the exact deviation of the signal allows one to subtract noise, obtained accurately from the signal by the same method using a sample lacking the fluorophore of interest. Thus, very small signals may be extracted from large amounts of noise because unitary data can be collected until each channel (signal) has good signal to noise characteristics.

The present invention utilizes photon counting as a means of quantifying fluorescence. The system contains two separate optical channels, one for monitoring signal plus noise (scattering and unwanted fluorescence), and the other for monitoring just noise. The two channels are separated optically but only one detection unit is used which is multiplexed back and forth between the two channels. With the use of an up/down counter, background or noise counts are subtracted from the signal counts automatically. The value of the fluorescent intensity displayed by the device is, therefore, the true fluorescent signal of the substance under investigation, in terms of number of photons per time of analysis.

The present invention is particularly useful in the analysis of fluorogenic substances and reaction products as an indicator of their concentration or of enzymatic activities. In other words, the invention provides an instrument capable of performing clinical assays and other assays of biochemically important substances. Certain requirements are placed on the invention when it is to be used for this purpose. First, sensitivity must be high enough to detect down to picomolar concentrations of fluorescent substance. Secondly, stability over extended periods of time is necessary. It should be apparent that the fluorescent signal received from a sample depends in part on the total amount of incident light flux. The incident flux level must therefore be held constant. Furthermore, when performing assays of substances wherein the fluorescent intensity is converted to concentration by reference to a standard curve, total instrument stability and most importantly incident light flux stability, is essential. The present invention presents a simple, novel method of assuring the constancy of incident flux and allows a measure of this to be used to normalize the results to an absolute reference.

For the purpose of illustrating the invention, there is shown in the drawing a form which is presently preferred; it being understood, however, that this invention is not limited to the precise arrangements and instrumentalities shown.

The sole FIGURE is a schematic representation of a photon counting fluorimeter showing the essential features of the present invention.

Referring now to the FIGURE in detail there is shown, in schematic form, a photon counting fluorimeter constructed in accordance with the principles of the present invention and designated generally as 10. The fluorimeter 10 is a double beam, single channel time-multiplex detection system utilizing a continuous tungsten lamp L1 as a light source. A filter 12 positioned adjacent the lamp L1 allows only a selected wavelength, such as ultraviolet, to pass through. Following the filter 12 is an aperture plate 14 which allows only a beam of ultraviolet light to pass. This reduces the amount of extraneous incident light and noise in the system.

After passing through aperture plate 14, the light beam is split into two substantially identical beams by mirror M1. One part of the beam is then reflected by mirror M2 and is directed toward a reference cell 16. The other of the two beams is reflected by mirror M3 and directed toward a sample cell 18. Sample cell 18 includes a sample of the substance being analyzed and reference cell 16 includes a similar sample but one which lacks the particular fluorophore of interest. A mechanical rotating chopper comprised of a chopper plate 20 rotated by a motor 22 is positioned adjacent mirrors M2 and M3 and functions to allow alternate illumination of the reference cell 16 and sample cell 18. In the preferred embodiment, motor 22 rotates at approximately 1800 RPM. Thus, reference cell 16 and sample cell 18 are alternately illuminated approximately 1800 times per minute. Chopper 20 is also arranged to alternately interrupt the light path between lamp L2 and photodiode PD1 and the light path between lamp L3 and photodiode PD2. Lamps L2 and L3 and photodiodes PD1 and PD2 are arranged such that photodiode PD1 generates a signal when reference cell 16 is illuminated and photodiode PD2 generates a signal when sample cell 18 is illuminated. As will be described in more detail hereinafter, the signals from photodiodes PD1 and PD2 are used to control various functions of the fluorimeter 10.

Positioned between reference cell 16 and sample cell 18 is a fourth mirror M4. Emitted light from each of the reference cell 16 and sample cell 18 is directed by mirror M4 to the photomultiplier tube 24. It should be noted that mirror M4 is arranged such that there is a 90° relationship between the excitation light and the emitted light to and from the reference and sample cells 16 and 18. This reduces the amount of incident or scattered light which reaches photomultiplier tube 24.

Photomultiplier tube 24 may be, for example an RCA 1P28. Photomultiplier tube 24 generates, at its output, an anode pulse for each photon impinging on the photocathode. These anode pulses are amplified by an amplifier 26 which may be, for example, an Ortec 454 timing filter amplifier. The output of amplifier 26 is then fed to a discriminator 28 such as an Ortec 436 100 MHz discriminator. The output of discriminator 28 is a series of standard pulses, each of which represents the detection of a single photon. The pulses from discriminator 28 are fed to an up/down counter 30 which may be, for example an Ortec 774 up/down counter.

An up/down selector circuit 32 connected to the up/down counter 30 causes the counter 30 to count up when a signal is generated by photodiode PD2 and causes counter 30 to count down when a signal is generated by photodiode PD1. In other words, the photons emitted by sample cell 18 and sensed by photomultiplier 24 are counted and added to the counter 30 and the number of photons emitted by reference cell 16 and sensed by photomultiplier tube 24 are counted and subtracted from the previous number in up/down counter 30. Since the light emitted from sample cell 18 includes signal plus noise (scattering and unwanted fluorescence) and the light emitted from reference cell 16 includes just noise, the difference between the two is the true fluorescent signal desired. Thus, after each completed cycle i.e. when the reference cell 16 and sample cell 18 have been illuminated the same number of times, the number in the up/down counter 30 will represent the true fluorescent signal in terms of the number of photons per time of analysis.

In order to insure that equal numbers of signals are received from reference cell 16 and sample cell 18, a signal from photodiode PD1 is fed to a gate 34 which controls up/down counter 30. Gate 34 turns up/down counter 30 on and off and can only function when a signal is received from photodiode PD1. Thus, when the device is turned on, counting will not begin until a signal is received from photodiode PD1 and when a particular analysis is being completed, the up/down counter 30 will not stop counting until the next signal from photodiode PD1. This feature ensures equal numbers of up counts and down counts during a test.

As pointed out above the fluorescent signal received from a sample depends to a great degree on the total amount of incident light flux. Furthermore, when performing assays of substances wherein the fluorescent intensity is converted to concentration by reference to a standard curve, incident light flux stability is essential. Thus, the output from any photon counting system should be a parameter which is referred to a constant signal strength or a known amount of total incident light flux. This is accomplished in accordance with the present invention by a novel source intensity monitor system shown substantially in the lower part of the FIGURE.

The source intensiy monitor system includes a fiber optic member 36 having a first end adapted to intercept a portion of the incident light from lamp L1. Fiber optic member 36 directs the sampled light to a third photodiode PD3. The output of photodiode PD3 is amplified by an operational amplifier 38 and the signal is then delivered to a voltage to frequency converter 40. The photodiode PD3 and operational amplifier 38 may be a single unit such as, for example, an E.G. & G. HUV1000. Voltage to frequency converter 40 preferably should generate TTL compatible pulses and may be, for example, a Burr Brown VFC-12. The number of pulses in the output of voltage to frequency converter 40 represents the amount of incident light from lamp L1 and these pulses are counted by a digital counter 42 such as a Fairchild 9350 six digit BCD counter. Once each cycle, i.e. once each rotation of chopper 20 as sensed by photodiode PD1, the count in counter 42 is transferred to a latch circuit 44 comprised, for example, of six Fairchild 9314 four digit latches. A suitable time is allowed for latch settling and thereafter the count in latch circuit 44 is compared in comparator circuit 46 to a number which is preset in thumbwheel switch 48. Comparator circuit 46 is preferably a 24 bit comparator such as a Fairchild 9324.

Once comparator 46 senses that the count in counter 42 is equal to the number preset in thumbwheel switch 48, a signal is sent to gate 34 to instruct the up/down counter 30 to stop counting. It will be recalled, however, that up/down counter 30 will not stop counting immediately but will continue to count until the next signal is received from photodiode PD1. If, on the other hand, comparator 46 does not show a favorable comparison i.e. the amount of incident flux sensed and counted by counter 42 has not reached the desired level preset in thumbwheel switch 48, the up/down counter 30 will continue to operate.

As shown at the bottom of the FIGURE, a count/inhibit circuit 50 is connected to counter 42. The inputs to count/inhibit circuit 50 are connected to photodiodes PD1 and PD2. Thus, counter 42 can be made to count continuously, to count only when a signal is received from photodiode PD1 or to count only when a signal is received from photodiode PD2. This provides a means for calibrating the instrument.

As previously stated, up/down counter 30 counts up whenever a signal is received from photodiode PD2 and counts down whenever a signal is received from photodiode PD1. It may, however, be desirable to have up/down counter 30 count only during part of the time that a signal is being received from photodiodes PD1 and PD2. For example, it may be desirable to avoid the transients at the beginning and end of each illumination of each of the reference and sample cells 16 and 18. In other words, it may, in some applications, be desirable to ignore photons reaching photomultiplier 24 during the short transition times as the incident light is applied to and removed from each of the reference and sample cells 16 and 18. This can easily be accomplished by having each of the photodiodes PD1 and PD2 energize a timed latch circuit such as a pair of one-shots which generate a pulse just after the beginning of a signal from photodiode PD1 or PD2 and which is timed to terminate just before the cessation of the signal from photodiode PD1 or PD2. These pulses can then be used to control the up/down counter 30 via the up/down select circuit 32. In this way, the transients at the beginning and end of the illumination of photodiodes PD1 and PD2 are removed and since the illumination of photodiodes PD1 and PD2 are timed with the illlumination of reference cell 16 and sample cell 18 the transients at the beginning and end of the illumination of these cells are also removed.

It should be noted that limitation on test run times, i.e. on the total time that counts can be accumulated in up/down counter 30, occurs from two different sources. If, for example, it is desired that the monitoring of incident flux to the sample and reference channels be better than one percent then minimum times are fixed by the chopper frequency. For one percent accuracy there must be at least 100 chopping cycles which represent a minimum accumulation time of three seconds for 1800 chopping cycles per minute. Maximum accumulation times are determined by the number of digits for the flux accumulation counter and the number of thumbwheel digits. Six digits and a 1 KHz pulse rate from the voltage to frequency converter dictate an upper limit in accumulation times of about ten minutes. This obviously can be extended by adding additional digits to the counter, latches, comparator and thumbwheel switch.

It should further be noted that while the invention has been described as being particularly applicable to the measurement of fluorescent light intensities it will work equally well for the measurement of phosphorescence, i.e. the emission of light after the cessation of light excitation. This can be easily accomplished by changing the timing such that light emitted from the reference cell 16 and sample cell 18 is detected after each of the cells is illuminated rather than concurrently with the illumination of each of the cells.

The present invention may be embodied in other specific forms without departing from the spirit or essential attributes thereof and, accordingly, reference should be made to the appended claims, rather than to the foregoing specification as indicating the scope of the invention.

We claim:

1. A photon counting fluorimeter including a source of incident light, comprising:

a sample cell containing a sample mixture with a fluorophore;

a reference cell containing said sample mixture without said fluorophore;

first means for illuminating said sample cell and said reference cell with light from said incident light source;

second means associated with both said sample and reference cells for separately detecting photons of light from said sample and reference cells and for generating a time division multiplexed series of uniform sample and reference pulses, each of said sample pulses representing a photon of light detected from said sample cell and each of said reference pulses representing a photon of light detected from said reference cell;

a third means for generating a signal representative of the number of said sample pulses relative to the number of said reference pulses generated by said second means including an up/down counter, means for causing said counter to count up when light is being received by said second means from said sample cell and means for causing said counter to count down when light is being received by said second means from said reference cell, sensing means for sensing the incident light, and means for stopping said counter from counting when said sensing means sense a predetermined amount of incident light.

2. A photon counting fluorimeter as claimed in claim 1 wherein said sensing means includes a photodetector means and a voltage to frequency converter, said voltage to frequency converter generating a number of pulses proportional to the amount of incident light sensed.

3. A photon counting fluorimeter as claimed in claim 2 wherein said means for stopping includes a means for storing a predetermined number and a comparator means for comparing at least a portion of the number of pulses generated by said voltage to frequency converter to said predetermined number, said comparator means generating a stop signal whenever said number of pulses compared by said comparator is equal to or greater than said predetermined number.

4. A method of measuring small quantities of a fluorescent substance in a mixture comprising the steps of:

providing a sample mixture including said fluorescent substance and a reference mixture substantially identical to said sample mixture but lacking said fluorescent substance;

illuminating said sample mixture;

illuminating said reference mixture;

separately detecting photons of light emitted from said sample and reference mixtures;

generating a time division multiplexed series of uniform sample and reference pulses, each of said sample pulses representing a photon of light detected from said sample mixture and each of said reference pulses representing a photon of light detected from said reference mixture, producing a signal representative of the number of sample pulses relative to the number of reference pulses, and sensing the amount of illuminating light flux and discontinuing the step of producing said signal representative of said number of sample pulses relative to the number of said reference pulses when the amount of illuminating light flux reaches a predetermined amount.

* * * * *

UNITED STATES PATENT AND TRADEMARK OFFICE
CERTIFICATE OF CORRECTION

PATENT NO. : 4,320,970
DATED : March 23, 1982
INVENTOR(S) : Dowben, et al.

It is certified that error appears in the above—identified patent and that said Letters Patent is hereby corrected as shown below:

On the cover page:

at item 76 after "James R. Bunting, 3146 Hudnall St., Dallas, Tex. 75235", insert --; Gordon D. Cumming, 25313 Via Oriol, Valencia, California 91355-- after item 76 insert---[73] Assignee: Diagnostic Reagents, Inc., Dallas, Texas 75205---

Signed and Sealed this

Third Day of April 1984

[SEAL]

Attest:

GERALD J. MOSSINGHOFF

Attesting Officer

Commissioner of Patents and Trademarks